United States Patent [19]

Parton

[11] Patent Number: 6,159,689
[45] Date of Patent: *Dec. 12, 2000

[54] METHODS OF CAPTURE AND ASSAY PROCEDURES

[75] Inventor: Adrian Parton, Exning, United Kingdom

[73] Assignee: Genera Technologies Limited, Cambridge, United Kingdom

[*] Notice: This patent is subject to a terminal disclaimer.

[21] Appl. No.: 09/074,648

[22] Filed: May 8, 1998

Related U.S. Application Data

[63] Continuation of application No. PCT/GB96/02744, Nov. 8, 1996.

[30] Foreign Application Priority Data

Nov. 10, 1995 [GB] United Kingdom ............... 9523045.4

[51] Int. Cl.⁷ .............................. C12Q 1/68; C12Q 1/02; G01N 33/53; G01N 33/554; G01N 33/532

[52] U.S. Cl. .............................. 435/6; 435/7.1; 435/7.2; 435/7.22; 435/7.32; 435/7.35; 435/7.5; 435/29; 435/38; 435/7.9; 435/174; 436/526; 436/544; 436/518; 436/806; 436/807

[58] Field of Search .................... 435/6, 4, 7.1, 7.2, 435/7.22, 7.32, 7.35, 7.5, 7.92, 29, 38, 174, 7.9, 239, 803; 436/526, 544, 518, 806, 807, 824

[56] References Cited

U.S. PATENT DOCUMENTS

| | | | |
|---|---|---|---|
| 5,076,950 | 12/1991 | Ullman et al. | 252/62.51 |
| 5,665,682 | 9/1997 | Kausch et al. | 435/181 |
| 5,741,462 | 4/1998 | Nova et al. | 422/68.1 |
| 5,821,066 | 10/1998 | Pyle et al. | 435/7.2 |
| 5,834,197 | 11/1998 | Parton | 435/6 |

FOREIGN PATENT DOCUMENTS

| | | |
|---|---|---|
| 297290 | 1/1989 | European Pat. Off. . |
| 0429794A2 | 6/1991 | European Pat. Off. . |
| 498920 A2 | 8/1992 | European Pat. Off. . |
| 0605003A2 | 7/1994 | European Pat. Off. . |
| 91/02083 | 2/1991 | WIPO . |
| WO 92/08133 | 5/1992 | WIPO . |
| WO 92/17609 | 10/1992 | WIPO . |
| 95/31726 | 11/1995 | WIPO . |
| 96/12960 | 5/1996 | WIPO . |
| WO 97/17611 | 5/1997 | WIPO . |

OTHER PUBLICATIONS

Fratamico et al. Food Microbiol. 9: 105–113, 1992.

Vermunt et al. J. Appl. Bacteriol. 72: 112–118, abstract, 1992.

Mullins et al. Microbiology 141: 2149–2156, abstract, 1995.

Kalle et al. Anal. Biochem. 208: 228–236, abstract, 1993.

Bifulco et al. Appl. Environ. Microbiol. 59: 772–776, abstract, 1995.

Deng et al. Appl. Environ. Microbiol. 63: 3134–3138, abstract, 1997.

*Primary Examiner*—James C. Housel
*Assistant Examiner*—S. Devi
*Attorney, Agent, or Firm*—Pillsbury Madison & Sutro LLP

[57] ABSTRACT

Methods of capturing and labeling a species, include attracting magnetically attractable particles to a solid support by magnetic forces, which particles have an affinity for the species, contacting the particles on the support with a sample containing the species to capture the species onto the particles on the support, and binding the species captured on the particles directly or indirectly to a detectable label before and/or whilst the species is captured on the particles on the support. The label may be bound to the captured species via an immunological binding partner which binds selectively to the species and may be a fluorescent label, luminescent label, enzyme label, dye label, phosphorescent label, metal-chelating label, radio label, spin label, heavy metal label, nucleic acid or nucleic acid analog hybridization label, avid or avid-like label suitably bound to or incorporated in particles which also bear a binding agent such as an antibody causing the particles to bind to the captured species.

14 Claims, 3 Drawing Sheets

METHODS OF CAPTURE AND ASSAY PROCEDURES

This is a Continuation of International Appln. No. PCT/GB96/02744 filed Nov. 8, 1996 which designated the U.S.

BACKGROUND OF THE INVENTION

1. Field of the Invention

The present invention relates to capturing species from samples and to assay procedures involving said species.

The term "species" is used herein generally to denote any material, organism or substance having specific characteristics and not in the taxonomic sense of the word, except where this is explicitly indicated.

Whilst the invention is of broad applicability, it is of particular relevance to the detection of micro-organisms.

2. Description of Related Art

In Patent Co-operation Application PCT/GB95/01056, as yet unpublished, we described a method of capturing a species from a sample by specific binding of the species to particles previously captured to a solid support by magnetic attraction. Examples of such particles were magnetic, antibody coated, plastics microparticles. It was indicated that species captured to such magnetically attractable particles could be assayed before or after removal from the solid support. Examples of assay techniques practised after removal of the particles from the solid support included immuno-fluorescent staining.

SUMMARY OF THE INVENTION

The present invention relates to an improvement in such procedures and provides a method of capturing and labelling a species, comprising attracting magnetically attractable particles to a solid support by magnetic forces, which particles have an affinity for said species, contacting said particles on said support with a sample containing said species to capture said species onto said particles on said support, and binding said species captured on said particles directly or indirectly to a detectable label before and/or whilst said species is captured on said particles on said support.

The label should not of course bind to the particles themselves, as there will be many such particles on the solid support which do not carry any of the captured species.

Preferably, said label is bound to said captured species via an immunological binding partner which binds selectively to said species. Many different forms of detectable label are known in the art and in general any of these may be used, including fluorescent labels, luminescent labels, enzyme labels such as horse radish peroxidase, alkaline phosphatase, glucose oxidases, galactosidases or ureases, dye labels, phosphorescent labels, metal-chelating labels such as iminodiacetic acid, ethylenediaminetetraacetic acid, diethylenetriaminepentaacetic acid or desferrioxamine B, radio labels, spin labels, heavy metal labels, nucleic acid or nucleic acid analogue hybridisation labels, avidin or avidin like labels such as streptavidin, or biotin. Amongst these however the labels which are visually detectable, e.g. under the light microscope, are especially preferred.

Preferably, said label is bound to or incorporated in particles which also bear a binding agent causing said particles to bind to the said captured species. This can greatly facilitate the linking of a detectable label to an immunological binding partner for use in the assay as all that generally will be required will be to take labelled particles such as fluorescent beads and to coat them with a suitable binding partner. The immunological binding partners for use in this invention include antibodies and also specific binding fragments of antibodies.

Optionally, the affinity of the captured particles for the species to be captured may be of a first level of specificity such that the desired species will be captured together with related species, and the level of specificity of the binding to the label may be higher so that only the desired species is labelled. If desired, two or more labels may be provided with different binding specificities so that more than one captured species may be labelled and discriminated in the assay.

By way of example, one may capture magnetically attractable beads coated with an first antibody which will recognise and bind any micro-organism within a range of taxonomic micro-organism species, e.g. any micro-organism within a particular genus, capture micro-organisms from a sample, and then label certain of the micro-organisms only with a detectable label by binding to the micro-organisms beads coated with a second antibody which will recognise only one or a limited sub-set within the range of taxonomic species recognised by the first antibody.

One may then observe binding of micro-organisms to the magnetically attractable particles which are not further labelled and also observe labelled micro-organisms.

This is of particular interest for instance in detecting Legionella of which there are numerous species, but only a restricted number including primarily *Legionella pneumophila* are known to cause legionaires disease. In assaying for Legionella in a sample of for instance cooling tower water it is of interest both to know whether Legionella of any species is present and to know whether in particular any of the Legionella present is *Legionella pneumophila*. This can readily be achieved according to the present invention by providing as the said first antibody an antibody which will bind any Legionella species and as the second antibody one which will bind only *L. pneumophila*. After eluting the beads from the solid support, one may then observe beads which have bound no micro-organism, beads which are carrying one or more micro-organisms but no label (if any species of Legionella was present), and beads which are complexed with a micro-organism and a labelled bead (if *L. pneumophila* was present). Similar methods may be applied to other micro-organisms.

If desired, the conditions in the apparatus used during the period of capture of micro-organisms to the magnetically bound particles and/or during the labelling of the captured micro-organisms may be arranged to favour culturing of the micro-organisms so as to increase the detectable population.

The label may be bound to the species to be assayed before said species is captured by the magnetically attractable particles on the support or during or after the capturing of the species. The retention of the species on the support via the magnetically attractable particles provides a ready way of separating excess label which may be washed away from the bound particles.

As in the case of the methods described in PCT/GB95/01056 generally, because the magnetically attractable particles are held on the solid support during the time in which they are being contacted with the liquid containing the species to be captured, it is possible for the volume containing the species to be much greater than the volume occupied by the particles during this operation. Large volumes of the liquid may be washed through or over the solid support bearing the magnetically attracted particles, so that the particles may capture said species in sufficient quantity for further operations to be carried out, even if the species is present at great dilutions in the liquid. For instance, the volume of the liquid contacted with the particles may be greater than the volume occupied by the solid support by a factor of at least 10, more preferably from 10 to 100 or more.

The liquid may be passed repeatedly over the solid support, e.g. by continuous recirculation, so as to improve the capture of said species. A liquid containing a suitable labelling reagent may then be circulated over the solid support in a similar way.

After labelling, the particles may be assayed for the captured species whilst retained on the solid support. It will generally however be more appropriate to release the particles with the captured species. This may be done simply by vigorous washing or even air blasting whilst maintaining the magnetic attraction but is preferably accomplished by reducing the magnetic attraction.

When the particles are released from the solid support, they may be collected in a much reduced volume of liquid, for instance a volume similar to that occupied by the solid support itself, or even less.

A very substantial concentration of the species to be captured may therefore be achieved.

The solid support may be a superparamagnetic material or ferromagnetic material. "Superparamagnetism" is the magnetic behaviour exhibited by materials which respond to a magnetic field with an induced magnetic field without resultant permanent magnetisation.

There are many examples of materials which exhibit superparamagnetism or ferromagnetism which may be used in the present invention. Particularly preferred materials are stainless steel, aluminium, chromium or platinum. Metallised foams based on such metals may be used, e.g. aluminium coated polyester/polyether foams which are commercially available.

However, materials in which an induced magnetic field results in a permanent residual field may also be used as further described below.

A solid support material may be magnetised to attract the magnetically attractable particles by placing the solid support within a suitable container and applying an external magnetic field from a permanent magnet or an electromagnet. The solid support, if of superparamagnetic material, may be demagnetised simply by turning off the electromagnet or physically removing the permanent magnet used so as to reduce the field. The magnetic field applied may be a rapidly reversing magnetic field obtained by passing an alternating current through a coil.

To prevent excessive heat generated in the coil of an electromagnet used for this purpose from reaching the solid support, the solid support may be positioned in a pole gap of a magnet core about which core a coil winding is positioned remote from the solid support.

A solid support material which is not superparamagnetic may be demagnetised by known methods such as gradual reduction and periodic reversal of an externally applied field.

Physically, the solid support may take many forms, e.g. mesh, wire, a wool, beads or one or more plates. The material preferably has an open structure to assist easy removal of the particles therefrom and easy passage on the liquid containing the species to be captured. Structures providing a substantial surface area within a small volume are preferred.

However, the solid support may be the walls of a container such as a glass tube to which the particles are attracted by an external magnetic field.

The most preferred form of solid support is a stainless steel mesh, e.g. of 40×40 wires per inch (16×16 wires per cm), used as a flat strip of single or double thickness.

Many forms of magnetically attractable particle are now known and easily commercially available. Examples include iron oxide particles as described in U.S. Pat. No. 4,554,088 and U.S. Pat. No. 3,917,538, nickel oxide particles as described in Biotec. and Bioengr. XIX: 101–124 (1977), Agarose-polyaldehyde beads containing magnetic particles as in U.S. Pat. No. 4,732,811. DYNAL beads (commercially available magnetic polystyrene coated beads); Magnogel 44 (magnetic polyacrylamide-agarose beads), ENZACRY (poly-M-diaminobenzene/iron oxide) as described in Clin. Chim. Acta. 69:387–396 (1976). Cellulose containing ferric oxide particles are described in Clin. Chem. 26:1281–1284 (1980) and albumin magnetic microspheres as described in J. IMMUNOL. Methods 53:109–122 (1982). Magnetic porous glass particles are described in WO-A-93/10162.

The particles may also be of superparamagnetic material.

The particles may preferably have a specific binding affinity for the species to be captured and for this purpose they may bear antibody molecules, substances having an epitope capable of reacting in a specific manner with an antibody such as an antigenic protein or oligosaccharide, biotin, avidin or streptavidin, or like materials. They may bear a nucleic acid or nucleic acid analogue such as DNA, RNA or a synthetic analogue thereof. Also, the particles may have a chemical rather than a biochemical affinity for the species to be captured. For instance, they may have chelating activity for capturing ions from the liquid.

They may have affinity for a water borne organism such as Legionella, cryptosporidium or Giardia. However, the invention is of general applicability and may be used for capturing a wide range of micro-organisms (e.g. Salmonella or Listeria) from a wide range of sample sources including food products and body fluid samples such as blood, serum, saliva, urine, cerebrospinal fluid and so forth.

The invention includes assay methods comprising capturing and labelling a species to be assayed or to be used in an assay by a method of capture as described above, and conducting an assay of or using said capture species based on said label. Optionally, the captured species may be removed from the particles prior to or during said assay procedure.

The assay procedures involved may take a wide variety of forms including chemical assay procedures, enzyme assay procedures such as RIA or ELISA or nucleic acid procedures such as hybridisation assays.

The assay may be an electro-rotation assay. WO-A-93/16383 describes apparatus in which electro-rotation assays can be conducted. As described there, particles such as plastics microbeads or the cells of organisms like yeast, Guardia and cryptosprodium can be made to rotate by the application of a rotating electrical field. The field conditions under which rotation is achieved, the direction of rotation and the speed of rotation, all depend upon the dielectric properties of the particle. Micro-organism cells can be concentrated by a capture method as described above and can then be detected by subjecting them to electro-rotation conditions and observing their electro-rotation or that of the particles to which they are bound. Where the micro-organisms are themselves rotatable, the magnetically attractable particles used in their concentration need not be removed prior to electro-rotation and indeed are an aid in observing the rotation, particularly where automated image analysis systems are used to perform the observation. The particle or particles bound to the micro-organisms provide a useful visual marker which can be seen rotating. Labels altering electro-rotation behaviour may be used as described in WO-A-93/16383.

BRIEF DESCRIPTION OF THE DRAWINGS

The invention will be further described and illustrated with reference to the accompanying drawings in which.

DETAILED DESCRIPTION

Figure 1:
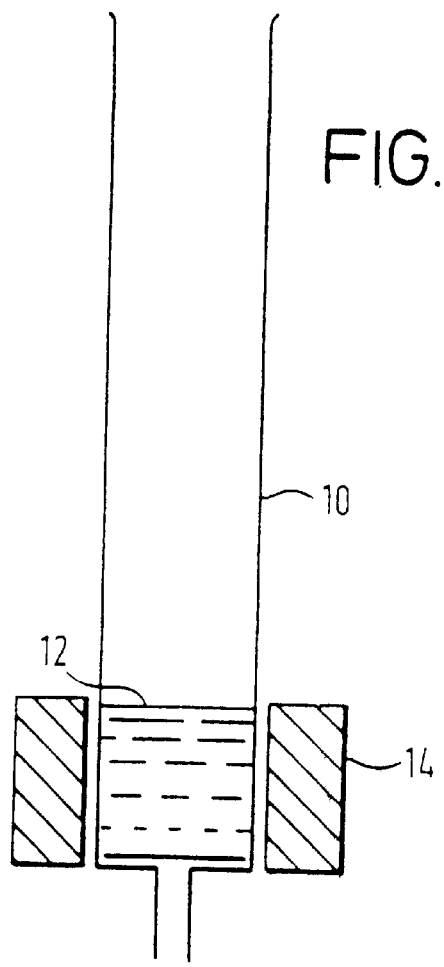
FIG. 1 shows schematical apparatus for use in the invention.
Figure 3:
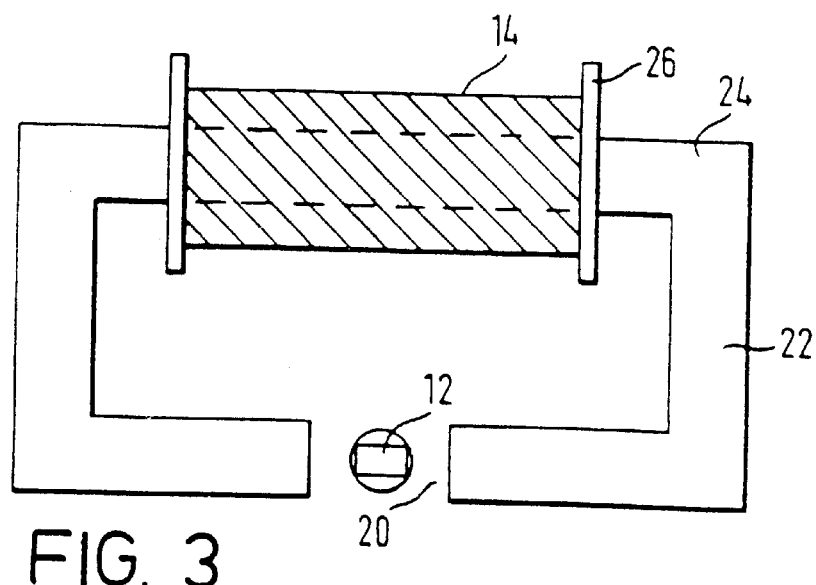
FIG. 3 is a plan view of the electromagnet in the apparatus shown in FIG. 2.

As shown in FIG. 1, apparatus for use in the invention may comprise a container such as a syringe body 10 containing a support matrix such as expanded aluminium 12 surrounded by a helically wound copper wire coil 14 which may for instance comprise 4000 turns of enamelled 40 SWG (standard wire gauge) wire to which is connected a suitable supply of alternating electric current e.g. a 50 volt 50 Hz supply, via suitable switch means. Generally, frequencies of from 1 to 500 volts may be employed at voltages from 1 to 500 volts.

In a typical procedure according to the invention, antibody coated magnetic beads in a suitable buffer (e.g. pbs) are exposed to the solid support and an external magnetic field is applied to induce a corresponding field in the solid support. Over a period of minutes, the particles are drawn on to the solid support. The attached particles may be washed by slowly running wash liquid into the top of the syringe body 10 whilst letting liquid out at a corresponding rate so as to avoid the level of liquid falling to expose the solid support.

If this were to happen, there would be a likelihood of surface tension forces pulling the beads off.

A sample containing organisms expressing surface antibodies corresponding to the antibodies in the beads and having a volume which may be of the order of 100 times the volume of the part of the syringe body 10 occupied by the solid support 12 may be slowly run through, optionally followed by further wash liquid, until the solid support is barely covered.

A reagent containing the label may then be slowly run through over the solid support.

The external magnetic field is then removed and the beads are permitted to detach from the solid support, optionally with agitation being used to disperse them. The beads may then be run out of the syringe for analysis, bearing any organisms which have bound thereto. An advantage of this procedure is that there is no need to use any chemical treatment to release the organisms from the solid support, which could affect the viability or integrity of the organisms. Chemical methods are, in contrast, normally needed in most immuno-affinity capture and release methods.

Figure 2:
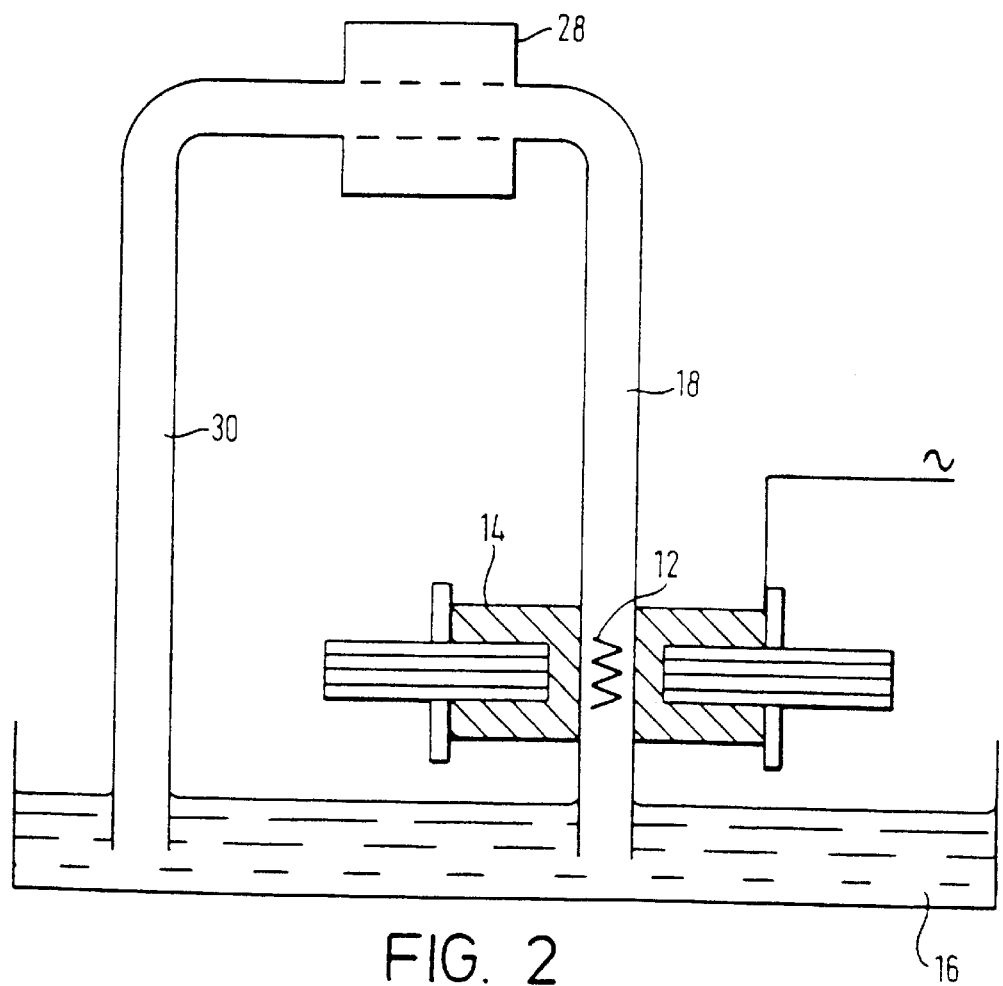
FIG. 2 shows a second form of apparatus for use in the invention.

An alternative form of apparatus shown in FIG. 2 comprises a reservoir 16 for liquid. A tube 18 dipping into the reservoir 16 contains the solid support 12 and passes through a pole gap 20 in a magnet core 22 which is C-shaped in plan view having a long arm 24 remote from the pole gap 20 around which is positioned a coil 14 wound on a coil former bobbin 26 and connected to an electrical supply as described in connection with FIG. 1. The tube 18 is connected via a peristaltic pump 28 to a further tube 30 dipping back into the reservoir 16.

In use, liquid to be treated in the system may be recirculated repeatedly using the peristaltic pump 28 to flow over the solid support 12 as described in more detail the examples below.

Figure 4:
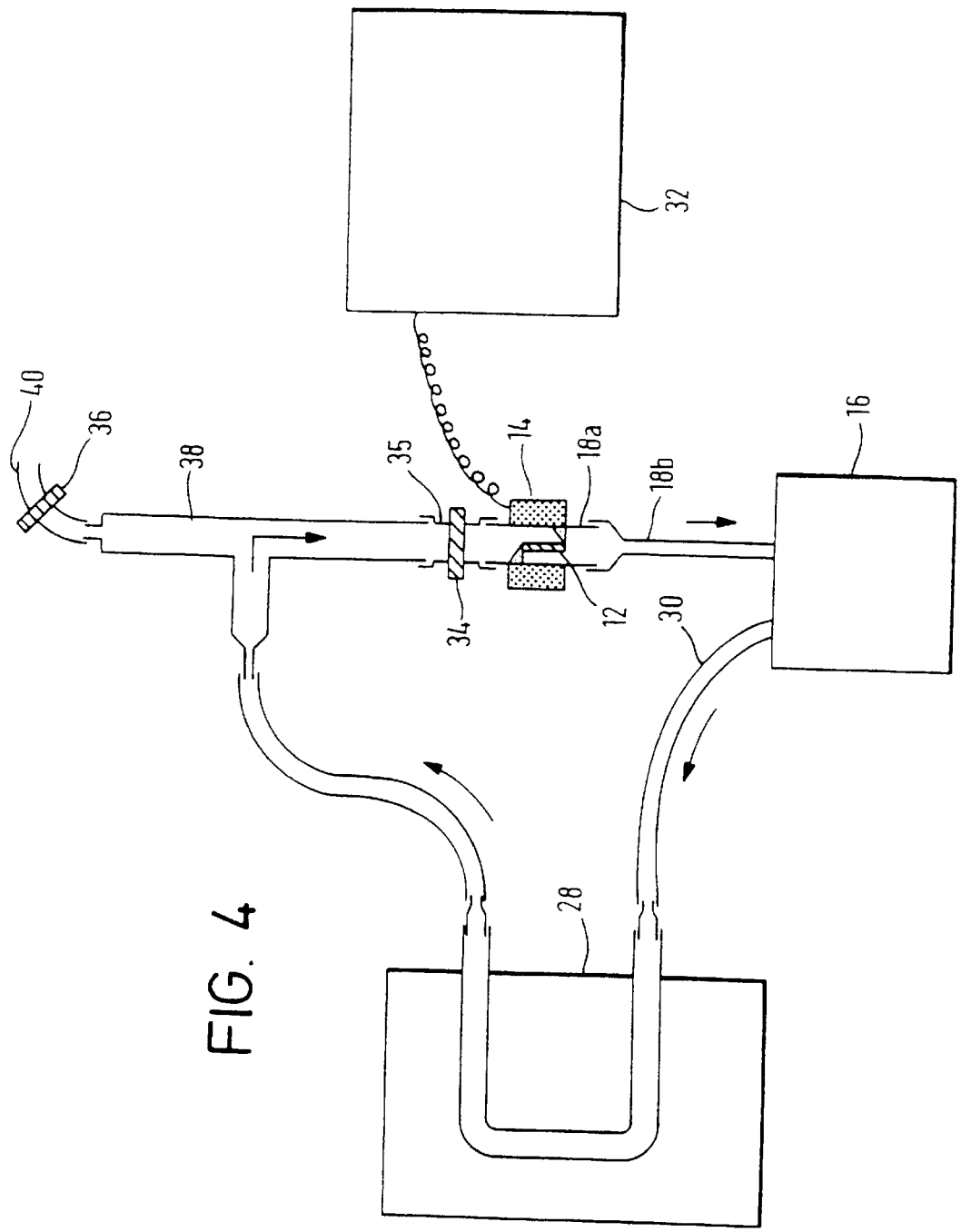
FIG. 4 shows a third form of apparatus for use in the invention.

A third form of apparatus is shown in FIG. 4 is similar to that of FIG. 2 except in the following respects. The tube 18 is divided into an upper larger diameter part 18a and a lower narrower diameter part 18b. The solid support 12 is contained in the part 18a. The coil is of 7000 turns of 0.2 mm insulated copper-wire on a bobbin of 4.5 cm length, 1.5 cm core diameter and 3.2 cm flange diameter, fitted over the tube 18a. The coil is run at a current of 10 to 150 mA, preferably about 75 mA, at a voltage of about 10 V from a power supply 32. Peristaltic pump 28 is connected to tube 18a by a side arm tube 38 which is joined to tube 18a via a flexible tube 35 fitted with a clip 34 by means of which it may be closed off during elution of magnetically held beads from the solid support.

At its upper end, side arm tube 38 forms a bubble trap which may be bled via a flexible tube 40 closed by a clip 36.

The invention will also be further illustrated by the following examples.

EXAMPLE 1

Formation of Legionella 0.1 $\mu$m Fluorescent Bead Complexes

The standard apparatus was set up as showing in FIG. 4. The operational procedure was carried out as follows:

The system was filled with PBS/0.05% Tween 20 by circulating the liquid around the apparatus and tapping the tubing to drive bubbles into the bubble trap.

Bead Coating

50 μl of paramagnetic beads (0.8 micron; 67% magnetic Sigma) were washed 3× using 0.45 micron filter sterilised PBS in a magnetic particle concentrator (Dynal MPC-1) and residual was liquid removed. The beads were then coated overnight with 1 ml of anti-Legionella antibody at 25 μg/ml using end over end rotation. They were then washed 3× as above and blocked with 1% BSA with 0.5% sodium azide being added as a preservative.

Magnetic Separation

500 μl of 0.8 micron paramagnetic beads (67% magnetic Sigma) with an NTU (nephelometery turbidity units) reading adjusted to 20 to standardise the number of beads coated as above were filtered through a 1 micron membrane and added to a plastic Universal containing 5 ml of PBS/Tween 20 and circulated at 160 ml/min. Bead binding was achieved using a steel mesh solid phase housed within plastic tubing and located within a coil carrying a current of 100 mA. After an hour the unbound beads were washed through by transferring the outlet tube to a waste beaker. The pump speed was then turned down to zero and the inlet and outlet tubes were transferred to a beaker containing 25 ml of Legionella cells suspended in PBS/Tween. Incubation of the sample was also for 1 hour at 160 ml/minute. After incubation, unbound sample was washed away by transferring the outlet tube to a waste beaker and allowing 500 ml of sterile PBS/Tween to pass through the system. At the end of the wash period the pump was turned down and the tubing inlet and outlet placed in a Universal containing 0.1 micron fluorescent beads coated by the same method as the paramagnetic beads but with washing being carried out in a microcentrifuge by means of 20 minute holding time at 13,000 RPM. These beads were circulated at 160 ml per minute for 1 hour and a normal bead wash repeated before the pump was switched off, the outlet tube was placed in a Universal and the tubing containing the solid phase detached from the rest of the tubing. With the power switched off, the bound beads were eluted using 20 ml of PBS squirted through the phase.

The eluent was filtered by passing it through a 1 micron puradisc (Whatman) and thereby trapping Legionella cells on the surface of the membrane. Legionella cells were recovered from the surface by back-sucking 1 ml of PBS through the membrane and then centrifuging this 1 ml volume. Legionella was identified using phase contrast optics and a X400 lens. Recovering date was based upon counts of random fields. Fluorescent beads attached to Legionella cells appeared red under TV light and with low transmitted light levels, combinations of phase and fluorescence could be used to show the Legionella cells and the beads respectively.

EXAMPLE 2

0.43 μm Beads

Example 1 was repeated except that the diameter of the fluorescent beads was 0.43 μm and the visualisation was conducted under green light (535 nm), the fluorescent beads attached to Legionella cells appearing red.

EXAMPLE 3

Simultaneous Capture of Legionella by Formation of Complexes with 0.43 μm Fluorescent Beads The standard apparatus was set up as shown in FIG. 4. The operational procedure was carried out as follows:

The system was filled with PBS/0/05% Tween 20 by circulating the liquid around the apparatus and tapping the tubing to drive bubbles into the bubble trap.
Bead Coating 50 μl of paramagnetic beads (0.8 micron; 67% magnetite; Sigma) were washed 3× using 0.45 micron filter sterilised PBS in a magnetic particle concentrator (Dynal MPC-1) and residual liquid removed. The beads were then coated overnight with 1 ml of anti-Legionella antibody at 25 μg/ml using end over end rotation. They were then washed 3× as above and blocked with 1% BSA with 0.5% sodium azide being added as a preservative.

0.43 micron fluorescent beads were coated in the same way, except that washes were carried out in microcentrifuge tubes by means of a twenty minute holding time at 13,000 RPM.
Magnetic Separation 500 μl of 0.8 micron paramagnetic beads (67% magnetic; Sigma) coated as above with an NTU reading adjusted to 20 were filtered through a 1 micron membrane and added to a plastic Universal containing 5 ml of PBS/Tween 20 and circulated at 160 ml/min. Bead binding was achieved using a steel mesh solid phase housed within plastic tubing and located within a coil carrying a current of 100 mA. After an hour the unbound beads were washed through by transferring the outlet tube to a waste beaker. The pump speed was then turned down to zero and the inlet and outlet tubes were transferred to a beaker containing 25 ml of Legionella cells suspended in PBS/Tween and 500 μl of 0.43 micron fluorescent bead suspension. Incubation of the sample and fluorescent beads was also for 1 hour at 160 ml/minute. After incubation, unbound sample and excess fluorescent beads were washed away by transferring the outlet tube to a waste beaker and allowing 500 ml of sterile PBS/Tween to pass through the system. At the end of the wash period the pump was turned down, and the outlet tube was placed in a Universal and the tubing containing the solid phase detached from the rest of the tubing. With the power switched off, the bound beads were eluted using 20 ml of PBS squirted through the phase.

The eluent was filtered by passing it through a 1 micron puradics (Whatman) and thereby trapping Legionella cells on the surface of the membrane. Legionella cells were recovered from the surface by back-sucking 1 ml of PBS through the membrane and then centrifuging this 1 ml volume. Legionella was identified using phase contrast optics and a X400 lens. Recovering data was based upon counts of random fields. Fluorescent beads attached to Legionella cells appeared red under green light (535 nm) and with low transmitted light levels, combinations of phase and fluorescence could be produced.

EXAMPLE 4

Formation of Salmonella Fluorescent Bead Complexes

The standard apparatus was set up as shown in FIG. 4. The operational procedure was carried out as follows:

The system was filled with PBS/0.05% Tween 20 by circulating the liquid around the apparatus and tapping the tubing to drive bubbles into the bubble trap.
Bead Coating 50 μl of paramagnetic beads (0.8 micron; 67% magnetic Sigma) were washed 3× using 0.45 micron filter sterilised PBS in a magnetic particle concentrator (Dynal MPC-1) and residual liquid removed. The beads were then coated overnight with 1 ml of anti-Salmonella antibody at 25 μl/mg using end over end rotation. They were then washed 3× as above and blocked with 1% BSA with 0.5% sodium azide being added as a preservative.
Magnetic Separation 500 μl of 0.8 micron paramagnetic beads (67% magnetic Sigma) coated as above with an NTU reading adjusted to 20 were filtered through a 1 micron membrane and added to a plastic Universal containing 5 ml of PBS/Tween 20 and circulated at 160 ml/min. Bead binding was achieved using a steel mesh solid Phase housed within plastic tubing and located within a coil carrying a current of 100 mA. After an hour the unbound beads were washed through by transferring the outlet tube to a waste beaker. The pump speed was then turned down to zero and the inlet and outlet tubes were transferred to a beaker containing 25 ml of Salmonella cells suspended in PBS/Tween. Incubation of the sample was also for 1 hour at 160 ml/minute. After incubation, unbound sample was washed away by transferring the outlet tube to a waste beaker and allowing 500 ml of sterile PBS/Tween to pass through the system. At the tend of the wash period the pump was turned down and the tubing inlet and outlet placed in a Universal containing 0.1 micron fluorescent beads coated by the same method as the paramagnetic beads but with washing being carried out in a microcentrifuge by means of 20 minute holding time at 13,000 RPM. These beads were circulated at 160 ml per minute for 1 hour and a normal bead was repeated before the pump was switched off, the outlet tube was placed in a Universal and the tubing containing the solid phase detached from the rest of the tubing. With the power switched off, the bound beads were eluted using 20 ml of PBS squirted through the phase.

The eluent was filtered by passing it through a 1 micron puradisc (Whatman) and thereby trapping Salmonella cells on the surface of the membrane. Salmonella cells were recovered from the surface by back-sucking 1 ml of PBS through the membrane and then centrifuging this 1 ml volume. Salmonella was identified using phase contrast optics and a X400 lens. Recovering data was based upon counts of random fields. Fluorescent beads attached to Salmonella cells appeared red under green light (5.35 nm) and with low transmitted light levels, combinations of phase and fluorescence could be produced.

The procedure was repeated using 0.43 μm fluorescent beads, coated with antibody as described above and similar results were obtained.

EXAMPLE 5

Demonstration of a Bead/Bead Assay for β-Galactosidase

The standard apparatus was set up as shown in FIG. 4. The operational procedure was carried out as follows:

The system was filled with PBS/0.05% Tween 20 by circulating the liquid around the apparatus and tapping the tubing to drive bubbles into the bubble trap.

Bead Coating

50 μl of paramagnetic beads (0.8 micron; 67% magnetic Sigma) were washed 3× using 0.45 micron filter sterilised PBS in a magnetic particle concentrator (Dynal MPC-1) and residual liquid removed. The beads were then coated overnight with 1 ml of anti-beta-galactosidase antibody at 25 μl/mg using end over end rotation. They were then washed 3× as above and blocked with 1% BSA with 0.5% sodium azide being added as a preservative.

0.43 micron fluorescent beads were coated in the same way, except that washes were carried out in microcentrifuge tubes by means of a twenty minute holding time at 13,000 RPM.

Magnetic Separation

500 μl of 0.8 micron paramagnetic beads (67% magnetic; Sigma) coated as above with an NTU reading adjusted to 20 were filtered through a 1 micron membrane and added to a plastic Universal containing 5 ml of PBS/Tween 20 and circulated at 160 ml/min. Bead binding was achieved using a steel mesh solid phase housed within plastic tubing and located within a coil carrying a current of 100 mA. After an hour the unbound beads were washed through by transferring the outlet tube to a waste beaker. The pump speed was then turned down to zero and the inlet and outlet tubes were transferred to a beaker containing dilutions of beta-galactosidase suspended in PBS/Tween. Incubation of the sample was also for 1 hour at 160 ml/minute. After incubation, unbound sample was washed away by transferring the outlet tube to a waste beaker and allowing 500 ml of sterile PBS/Tween to pass through the system. At the end of the wash period the pump was turned down, and the tubing inlet and outlet tubes placed in a Universal containing 500 μl fluorescent beads suspended in 5 ml of PBS/Tween. After incubation of the sample for 1 hour at a circulation rate of 160 ml/minute, the wash step was repeated and at the end of the wash the pump was turned down, the outlet tube was placed in a Universal and the tubing containing the solid phase detached from the rest of the tubing. With the power switched off, the bound beads were eluted using 20 ml of PBS squirted through the phase.

The beads were filtered on to a 0.45 membrane and the membrane scanned under a combination of fluorescent and transmitted light for red beads attached to magnetic non-fluorescent beads.

Many modifications and variations of the invention as illustrated and described above are possible within the broad scope of the invention. In particular, the invention may be applied to a wide range of analyte species. It will be of particular benefit where the analyte species is dilute and/or present in association with large amounts of particulate material, e.g. in the food industry for detecting organisms in foodstuffs such as cheese.

What is claimed is:

1. A method of capturing and labelling a species, comprising first attracting magnetically attractable particles to a solid support by magnetic forces, which particles have an affinity for said species, then contacting said particles on said support with a sample containing said species to capture said species onto said particles on said support, and binding said species captured on said particles directly or indirectly to a detectable label before and/or whilst said species is captured on said particles on said support.

2. A method as claimed in claim 1, wherein said label is bound to said captured species via an immunological binding partner which binds selectively to said species.

3. A method as claimed in claim 1 or claim 2, wherein said label is an enzyme label, a metal-chelating label, a radio label, a spin label, a heavy metal label, avidin or a label having specific binding affinity to biotin, or biotin.

4. A method as claimed in claim 1, wherein said label is a fluorescent label, a luminescent label, a dye label, or a phosphorescent label.

5. A method as claimed in claim 4, wherein said label is visually detectable.

6. A method as claimed in claim 1, wherein said particles have affinity for said species of a first level of specificity and said label is bound to said species via a binding partner having a second, higher level of specificity for said species.

7. A method as claimed in any preceding claim, wherein a sample containing said species is recirculated over said particles on said support to pass thereover repeatedly to capture said species on to said magnetically attractable particles on said solid support.

8. A method as claimed in any preceding claim, wherein said solid support is of superparamagnetic or ferromagnetic material and said magnetic forces are produced in said material by the application of a magnetic field.

9. A method as claimed in any preceding claim, wherein said magnetic field is produced by an electromagnet and said magnetic forces are reduced by deactivation of said electromagnet.

10. A method as claimed in any preceding claim, wherein said magnetically attractable particles are ferromagnetic or superparamagnetic particles.

11. A method as claimed in any preceding claim, wherein said particles bear an antibody, a substance having an epitope capable of reacting in a specific manner with an antibody, a nucleic acid, biotin, or avidin or streptavidin, with which to capture said species.

12. A method as claimed in claim 1, wherein said species to be captured is a microorganism.

13. A method as claimed in any preceding claim, further comprising releasing said particles from said support by reduction of said magnetic forces.

14. An assay method comprising capturing and labeling a species to be assayed or used in an assay, by a method as claimed in claim 1, and conducting an assay based on said label of said captured species or conducting an assay based on said label using said captured species.

* * * * *